(12) United States Patent
Kindlein

(10) Patent No.: US 7,229,401 B2
(45) Date of Patent: Jun. 12, 2007

(54) SELF CONTROLLED IMAGE GUIDED DEVICE AND METHOD FOR INSERTING A NEEDLE IN AN ANIMAL BODY FOR EFFECTING RADIATION THERAPY IN SAID BODY

(75) Inventor: Johann Kindlein, Oberhausen (DE)

(73) Assignee: Nucletron B. V., Veenendaal (NL)

( * ) Notice: Subject to any disclaimer, the term of this patent is extended or adjusted under 35 U.S.C. 154(b) by 646 days.

(21) Appl. No.: 10/301,791

(22) Filed: Nov. 22, 2002

(65) Prior Publication Data

US 2003/0100814 A1 May 29, 2003

(30) Foreign Application Priority Data

Nov. 23, 2001 (EP) .................................. 01204555

(51) Int. Cl.
*A61M 36/12* (2006.01)
*A61M 31/00* (2006.01)
*A61B 19/00* (2006.01)

(52) U.S. Cl. .............................. 600/7; 600/8; 600/417; 600/429; 604/57; 606/108; 606/130

(58) Field of Classification Search ...................... None
See application file for complete search history.

(56) References Cited

U.S. PATENT DOCUMENTS 5,056,523 A * 10/1991 Hotchkiss et al. .......... 600/427
5,280,427 A * 1/1994 Magnusson et al. ........ 600/407
5,938,583 A    8/1999 Grimm
6,129,670 A   10/2000 Burdette et al.
6,311,084 B1  10/2001 Cormack et al.
6,400,979 B1 * 6/2002 Stoianovici et al. ........ 600/427
6,546,279 B1 * 4/2003 Bova et al. .................. 600/429

FOREIGN PATENT DOCUMENTS

EP    1 070 519 A1   1/2001
WO    WO 01/28631 A1  4/2001

* cited by examiner

*Primary Examiner*—Glenn K. Dawson
(74) *Attorney, Agent, or Firm*—Birch, Stewart, Kolasch & Birch, LLP

(57) ABSTRACT

The invention relates to a device and method for inserting a needle in an animal body for effecting radiation therapy in the body, including a template for positioning the needles to be inserted, needle drive structure for drive a needle through said template towards a desired location in the body, and real-time imaging structure for creating and presenting an image of the desired location and the position of said needle during the insertion of said needle. Due to the fact that the bevelled tip of a hollow needle cause the needle to diverge away from the "line of insertion or movement" and away from the actual desired position in the animal body adversely affecting the dosimetry quality of the implanted seeds a more accurate insertion of the needle is required. According to the invention the device is provided with adjusting structure for adjusting a movement of said needle towards said desired location during insertion.

20 Claims, 5 Drawing Sheets

SELF CONTROLLED IMAGE GUIDED DEVICE AND METHOD FOR INSERTING A NEEDLE IN AN ANIMAL BODY FOR EFFECTING RADIATION THERAPY IN SAID BODY

This nonprovisional application claims priority under 35 U.S.C. § 119(a) on Patent Application No. 01204555.5 filed in EUROPE on Nov. 23, 2001, which is herein incorporated by reference.

DESCRIPTION

The invention relates to a device and method for inserting a needle in an animal body for effecting radiation therapy in said body, comprising a template for positioning the needles to be inserted, needle drive means for drive a needle through said template towards a desired location in the body, and real-time imaging means for creating and presenting an image of the desired location and the position of said needle during the insertion of said needle.

It is noted that the device and method according to the invention as described in this application can be used for each medical application, wherein a needle is to be inserted into an animal body using imaging means. For example, the device and method described in this patent application can be used as biopsy devices, and for any other devices wherein High Dose Radiation or Low Dose Radiation therapy is applied to an animal body, for example the radioactive seed implant treatment of prostate cancer.

There are three fundamental treatments for prostate cancer, including radical prostatectomy (surgery), external radiation by means of high energy electro-magnetic beams and radioactive seed implantation. Radical prostatectomy has historically been very effective, but also has a relatively high rate of impotence, incontinence and surgical morbidity associated with it. External beam radiation has been reasonably effective for treatment of early stages of prostate cancer and has fewer side affects than radical prostatectomy. Beyond the early stages of the disease, however, external beam radiation decreases in effectiveness relative to the surgical procedure.

The third technique, radioactive seed implantation, involves the placement of radioactive seed-like elements in the prostate gland. The radioactive seeds deliver high dosages of radiation to the prostate, but relatively low dosages to the surrounding tissue, such that the radiation is quite targeted to the prostate, resulting in the destruction of cancer cells in the prostate before they can spread to other parts of the body.

An example of radioactive seed implant treatment of prostate cancer according to the introduction above is for example disclosed in the European patent application no. EP-A1-1 070 519 filed by the same applicant. With this technique, also known as brachytherapy, it is possible to treat a patient outdoors instead of at the hospital and the patient can resume his normal activities just a couple of days after the treatment. The technique has proven to have relatively low incontinence and impotency rates and therefore has become increasingly attractive, and has become more implemented than surgery (radical prostatectomy).

With the device and method according to EP-A1-1 070 519 hollow needles are inserted in the prostate gland under guidance of imaging means, e.g. ultrasound using an ultrasound probe, which probe is introduced into the rectum. A more accurate position of the needles can be obtained by using a template provided with a plurality of guiding holes for the implant needles. Under fluoroscopy the positions of the needles are checked. Once the hollow needles are inserted at their desired locations in the prostate gland radioactive seeds are inserted into said hollow needles. The number and relative positions of said seeds are determined and calculated in accordance with a preplanned dosimetry pattern using a doses planning therapy system.

Once the radioactive seeds are implanted into the hollow needles, said needles are retracted from the body leaving the implanted seeds in the prostate gland for radiating the cancer cell by means of natural radioactive decay.

A drawback of said technique can be found in the tips of the hollow needles or stylets, which tips have bevelled portions causing the needles to diverge away from the "line of insertion or movement" and away from the actual desired positions in the prostate gland. This affects the dosimetry quality of the implanted seeds, when the needles deviate from their orientations as planned prior to the treatment.

Said needle diverging can be monitored with said imaging means by medical personnel, which can correct said deviation by retracting the needle over a small distance and reinserting the needle along its correct "line of insertion". If retracting the needle slightly and reinserting it is not successful, it may be necessary to guide the needle in the proper direction by applying slight pressure with a finger as proposed in U.S. Pat. No. 5,938,583.

Nonetheless, a perfect match of the implanted needles with the desired, planned dosimetry pattern is not always possible due to many reasons. Medical personnel may accept a deviation of an inserted needle from its desired location in the prostate. Furthermore anatomical and spatial constraints may also prevent a needle from reaching its desired location in the prostate gland. Needle divergence degrades the dosimetric quality of the implanted seeds: the minimum target dose, the target dose coverage and therefore the tumour biological effective dose may significantly decrease.

It's an object of the invention to provide a more accurate device and method for inserting a needle in an animal body for effecting radiation therapy in said body, wherein according to the invention the device is characterized in that further means are present for adjusting the movement of said needle towards said desired location during insertion.

More especially said adjusting means adjust the movement of said needle based on signals delivered by said imaging means. With this improved device a more accurate insertion of needles in an animal body can be obtained, wherein any deviation of the needle during insertion is corrected and adjusted automatically by the device according to the invention, resulting in an implanted needle with a more accurate match with its desired location.

More in particular said adjusting means are capable of exerting correction forces on said needle almost perpendicular to the direction of insertion, and especially said adjusting means are capable of moving said needle in a direction perpendicular to the direction of insertion. Especially said adjusting means can move said needle in two orthogonal directions, wherein said adjusting means comprise at least one drive means for moving said needle in at least one of said directions. Herewith, it is possible to correct for any deviation of the inserted hollow needle towards the actual desired location.

A specific embodiment of the device according to the invention is characterized in that said adjusting means comprise a shaft connected to at least one drive means, which shaft is provided at its free end with a guide ring through which the needle to be inserted is guided. More in particular said guide ring comprises at least two ring parts, which parts can be moved in order to be released from or to placed around the needle to be inserted.

With an embodiment wherein automatically a new needle to be inserted in the patient's body said shaft has a hollow, longitudinal bore through which an actuator rod is movably mounted for actuating said at least two ring parts, said actuator rod is connected with one end of each of said at least two ring parts. For releasing a needle just inserted in the patient's body said actuator rod is moved in the direction towards the needle, such that the free ends of said ring parts are moved away from each other.

To bring a new needle to be inserted in co-operating contact with the adjusting means said actuator rod is moved in the direction away from the needle, such that the free ends the ring parts are moved towards each other. Thereby said at least two ring parts can abut against a cam mounted near the free end of said shaft.

In a specific embodiment the template used to insert the needle at a first position or orientation with respect to the animal body is made of a flexible rubber, material, e.g. silicone. Therefore already known templates provided with a plurality of uniformly spaced apart guide holes for the needles to be inserted are no longer needed. By replacing such specially constructed and expensive templates by a template without guide holes a less constricted optimization method is obtained and the exact position of the needles determined with a real inverse brachy-therapy planning system can be steered by the motorized template-needle insertion means.

For providing a counter force on the needle, for example as a result of the flexibility of the rubber template near at least one side of said template a metal plate is positioned, provided with a plurality of holes.

Furthermore, the insertion of the needle is terminated once the needle is inserted at the desired location in the body.

The invention also relates to a method for inserting at least one hollow needle to a desired location in an animal or human body for use in radioactive seed implant treatment of cancer, comprising the steps of positioning a needle near the animal body, inserting said needle towards the desired location in the body, and imaging the desired location and the position of said needle during the insertion of said needle using real-time imaging means, wherein according to the invention the method comprises the further step of adjusting the insertion of said needle towards said desired location during insertion.

Furthermore signals are delivered by said imaging means used for adjusting the insertion of said needle.

The invention shall now be described in more detail with reference to the accompanying drawings, in which.

It is to be noted that the following detailed description will be made with respect to treatment of a prostate gland. However, the device and method according to the invention can be used for each medical application, wherein a needle is to be inserted into an animal body using imaging means. The device and method described in this patent application can also be used as biopsy devices, and in far more applications wherein High Doses Radiation or Low Doses Radiation therapy is applied to an animal body. Therefore the description below should be regarded as an illustration for one specific application and not as a limitation of the invention.

Figure 1:
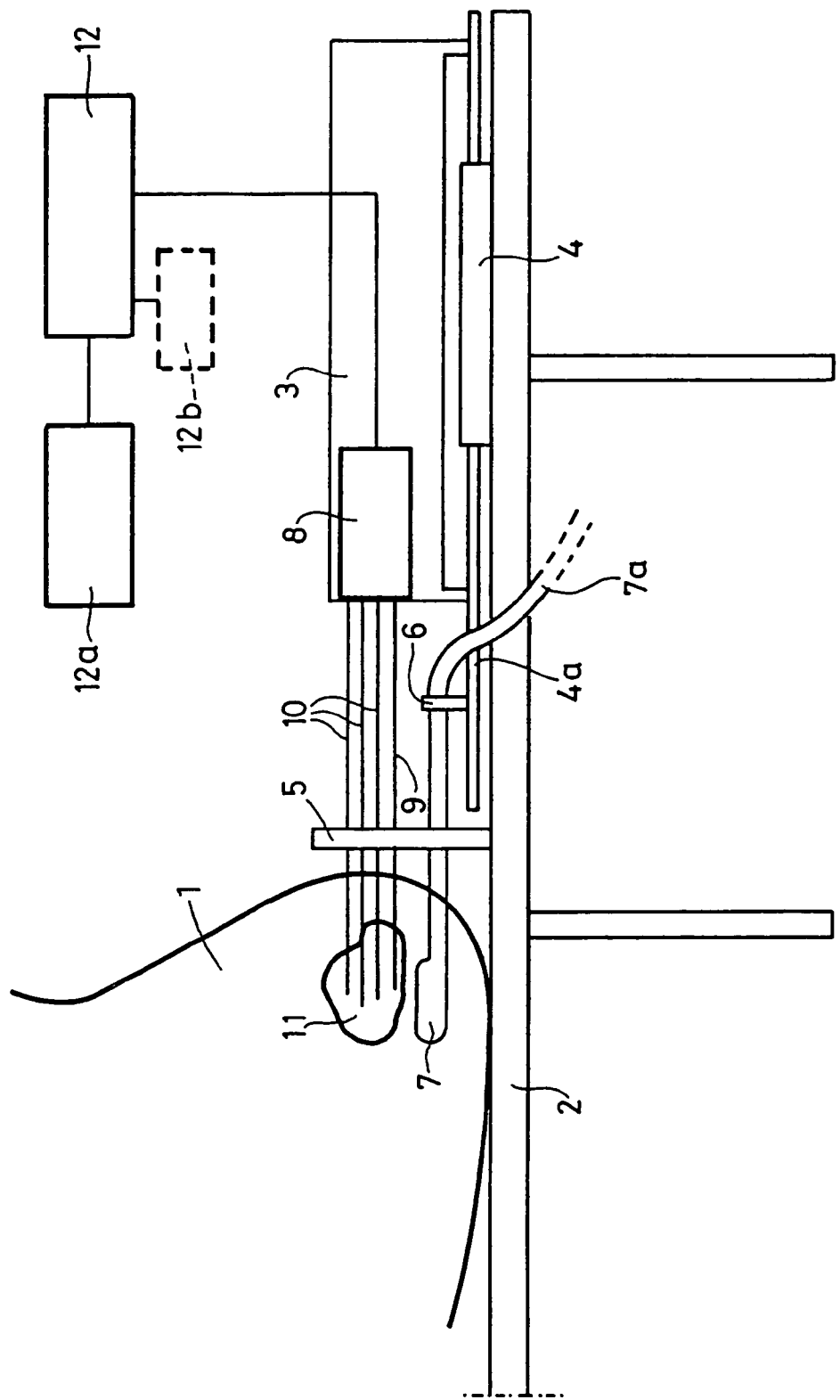
FIG. 1 shows a schematic and simplified device according to the state of the art.

FIG. 1 shows in very schematic form various elements of a known device for implanting radioactive seeds into a prostate gland. A patient 1 is shown lying in lithotomy position on a table 2. Fixedly connected to the table 2 is a housing 3. Housing 3 comprises a drive means 4 to move rod 4a stepwise. A template 5 is connected or mounted to the table 2, which template is provided (not shown) with a plurality of guiding holes through which holes hollow needles 9, 10 can be positioned relative to the patient. By means of a holder 6 a transrectal imaging probe 7 is fixedly connected to said rod 4a, which is moveable in a direction towards and from the patient by means of the drive means 4. The imaging probe 7 can be an ultrasound probe.

A needle 9 is used for fixing the prostate gland 11 in position relative to the template 5. A number of needles 10 is fixed into position through the template 5 in the prostate gland 11. The template 5 determines the relative positions of the needles 10 in two dimensions. The needles 10 are open at their distal ends and are sealed of by a plug of biocompatible, preferably bio-absorbable wax. In said housing 3 a seed loading unit 8 is present.

A well-known therapy planning module 12a is provided for determining the number and relative positions of seeds in each needle for implantation in the prostate gland 11. Such therapy planning module 12a usually comprises a computer programmed with a therapy planning program. The therapy planning module 12a is connected to the seed loading unit 8 through a control device 12 for controlling the number of seeds for each needle. Control device 12 may be a separate device or may be an integrated part either of the seed loading unit 8 or of the therapy planning module 12a or may be embodied in the software of the therapy planning module 12a or of the seed loading unit 8.

The known device shown in FIG. 1 operates as follows. A patient 1 is under spinal or general anesthesia and lies on the operating table 2 in lithotomy position. The (ultrasound) imaging probe 7 is introduced into the rectum and the probe is connected via signal line 7a with a well known image screen, where an image may be seen of the inside of the patient in particular of the prostate gland 11 as seen from the point of view of the imaging probe 7. The template 5 is attached to the drive means 4, thereby insuring the correlation of the ultrasound image geometry and the template 5. The prostate gland 11 is fixed relative to the template 5 and the drive means 4 and the imaging probe 7 by means of one or more needles 9, 10. Subsequently further needles 10 are introduced in the body and the prostate gland under ultrasound guidance one by one.

Moving the imaging probe with the drive means 4 longitudinally within the rectum controls the needle depths of each needle 10. After all needles 10 have been placed, their positions relative to the prostate gland 11 are determined in at least one of several known ways. In a known way the therapy planning module 12a determines how the needles 10 are to be placed in the prostate and how many radioactive seeds are to be placed in what order in each of the needles 10. The information about the desired placement of the radioactive seeds in the needles 10 is used to control the seed loading unit 8.

Usually the seeds are spaced from each other by spacers. For example seeds of 0.5 cm length may be spaced by spacers also of 0.5 cm length. Other measures of seeds and spacers are imaginable. A set of seeds and spacers loaded or to be loaded into a needle will be called a seed train or a train of seeds or a seed-spacer train. For each needle 10 the configuration of an applicable seed-spacer train is determined by the therapy planning module 12a. The seed loading unit 8 is controlled by the control device 12 to make up a seed-spacer train for each needle 10. Once a seed-spacer train is to be or has been made up for a specific needle a connection is made to the specific needle. After the seed-spacer train has been made up it is urged into the specific needle by a pushing drive (not shown) that is part of the seed loading unit 8.

Since all elements of the seed loading unit 8 and the needles 10 and their interconnections are of specific pre-known dimensions, which may or may not be the same for all like elements and such dimensions have been made known, e.g. pre-loaded in or pre-entered via a keyboard 12b to the control device 12 the pushing drive pushes with a pushing wire the seed-spacer train just until it reaches the distal end of the specific needle. Subsequently the pushing wire is fixed in position and the specific needle is retracted over a distance equal to or slightly greater than the length of the seed-spacer train in it. Thereby the wax plug and the seed-spacer train are introduced in the prostate gland 11.

Next the pushing wire is withdrawn into the seed loading unit 8 for pushing a next seed-spacer train into the prostate gland 11. The delivery of seed-spacer trains in the prostate gland continues until each needle 10 has been retracted and a number of seed-spacer trains equal to the number of needles 10 has been delivered in the prostate gland 11. Subsequently the needles 10 are retracted from the patient completely. After the geometry of the implanted seeds has been checked under fluoroscopy or another method of checking the presence of the seeds in the prostate gland 11 and removal of the ultrasound probe 7 the patient 1 is hospitalized for recovery.

A known drawback of the known device can be found in the tip of the hollow needles or stylets used, which tip has a bevelled portion causing the needle to diverge away from the "line of insertion or movement" and away from the actual desired position in the prostate gland. This affects the dosimetry quality of the implanted seeds, when the needles deviate from their orientations as planned prior to the treatment. Said needle diverging can be monitored with said imaging means by medical personnel, which can correct said deviation by retracting the needle over a small distance and reinserting the needle along its correct "line of insertion". If retracting the needle slightly and reinserting it is not successful, it may be necessary to guide the needle in the proper direction by applying slight pressure with a finger.

Nonetheless, a perfect match of the implanted needles with the desired, planned dosimetry pattern is not always possible due to many reasons. Medical personnel may accept a deviation of an inserted needle from its desired location in the prostate. Furthermore anatomical and spatial constraints may also prevent a needle from reaching its desired location in the prostate gland. Needle divergence degrades the dosimetric quality of the implanted seeds: the minimum target dose, the target dose coverage and therefore the tumour biological effective dose may significantly decrease.

Figure 2:
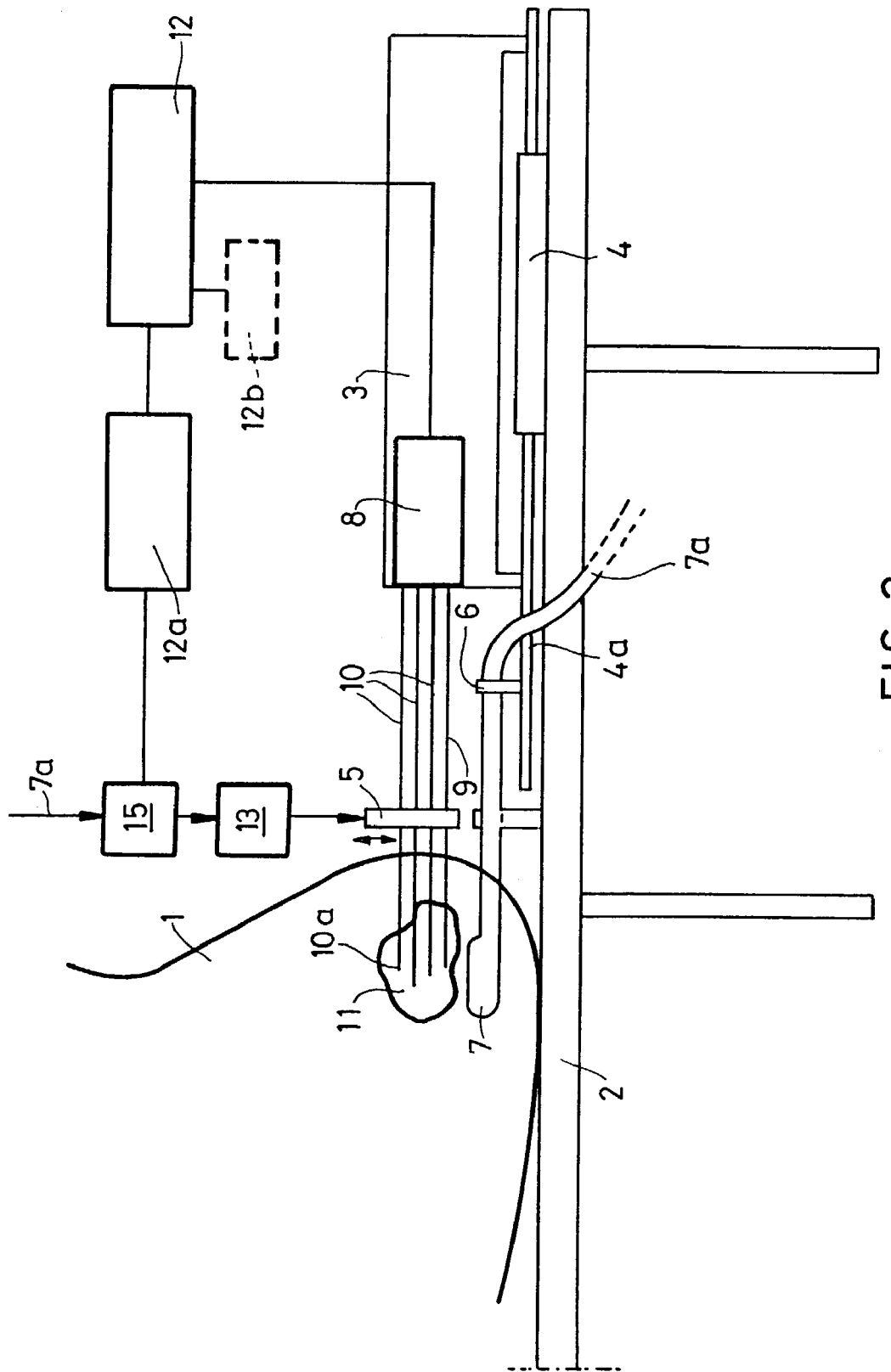
FIG. 2 shows a schematic view of an embodiment of a device according to the invention.

In FIG. 2 an embodiment of a device according to the invention is schematically depicted, which device obviates the above drawbacks. For the sake of clarity corresponding parts of the devices of FIGS. 1 and 2 have been given the same reference numerals.

In order to obtain a more accurate insertion of the hollow needles 10 matching more closely the desired, planned dosimetry pattern the embodiment of the device according to the invention as disclosed in FIG. 2 is provided with further means 13 which adjust the movement of the needle 10 to be inserted towards the desired location in the prostate gland 11.

More in particular the adjusting means are arranged such that they are capable of adjusting the movement of the needle 10 to be inserted into the prostate 11 using signals 7a delivered by the imaging means 7.

These features of the invention are described in more detail with reference to FIGS. 3, 4 and 5, wherein also for the sake of clarity corresponding parts are indicated by the same reference numerals.

Figure 3:
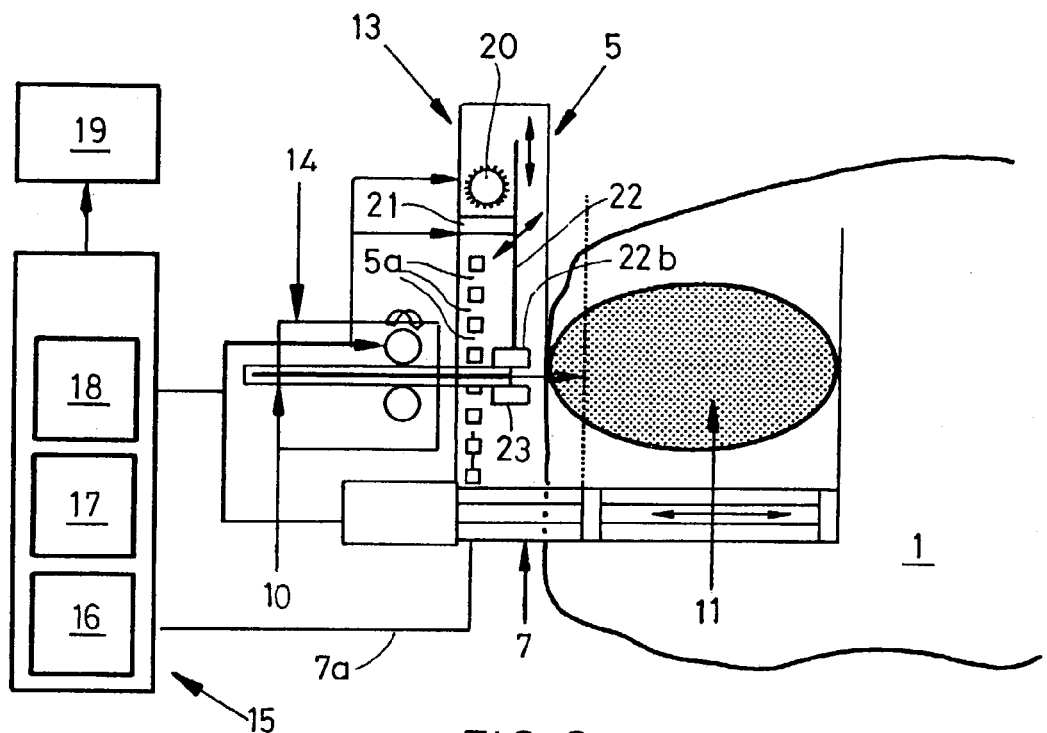
FIGS. 3-6 show schematic views in more detail of the embodiment as shown in FIG. 2.

FIG. 3 discloses the (ultrasound) imaging probe 7 inserted into the rectum of the patient for obtaining an image of the inside of the patient and in particular of the prostate gland 11. Said image is transmitted via signal line 7a towards signal processing means 15 which contains frame grabber means 16, image analysing means 17 and control means 18. Furthermore, the signal processing means 15 are connected to a well-known screen 19 for displaying the image taken by the ultrasound imaging probe 7.

The probe 7 accumulates image data from a treatment region or organ of the patient 1, which image data is processed using two-dimensional image information in a small defined area in which the tip 10a of the needle 10 to be inserted is expected. The image is stored in suitable storage means (not shown) present in the signal processing means 15 and the needle insertion means 14 will insert the needle 10 automatically until the tip 10a of the needle 10 will appear in the ultrasound image taken continuously by the probe 7. The new image area with the needle image will be analysed again and the needle tip 10a is detected automatically with a special scanning detection algorithm present in said image analysing means 17 by comparing each pixel information in the selected area of both images taken before and after the advancement of the needle 10. The pixel information from the first image is substracted from the pixel information from the second image, and the needle image will be detected automatically and the location of the detected needle image will be compared with the prescribed needle location.

If no differences are detected between the prescribed and the achieved needle position the probe 7 will move to the next position in the patient's body 1, and a new image will be made and stored and without effecting any pressure on the needle 10 during the insertion the needle tip 10a will be moved towards the new position and the analysing process will be repeated as described before.

Thus, in the signal processing means 15 the image delivered by the ultrasound imaging probe 7 and more in particular the exact location of the needle 10 in the prostate gland 11 during insertion by the needle insertion means 14 is analysed. Any deviation of the needle 10 from its desired orientation, as planned prior to the treatment by the therapy planning module 12a can be easily determined. In order to correct for such deviation the signal processing means 15 are also fed with information from the therapy planning module 12a concerning the planned desired location of the needle 10 in question.

Using the actual orientation of the needle 10 in the prostate gland 11 as imaged by the probe 7 and the desired orientation as planned by the therapy planning module 12a the signal processing means 15 starts to control the adjusting means 13 using the control means 18 in order to correct the deviation of the inserted needle 10 towards its "desired line of insertion or movement".

If the needle 10 will not achieve the prescribed position the image analysing means 17 and the control means 18 will start to control the adjusting means 13, which means 13 exercise a well calculated and directed pressure on the needle 10 to correct the direction of movement of the needle. The adjusted direction of the needle will move the needle into the prescribed position.

Figure 4:
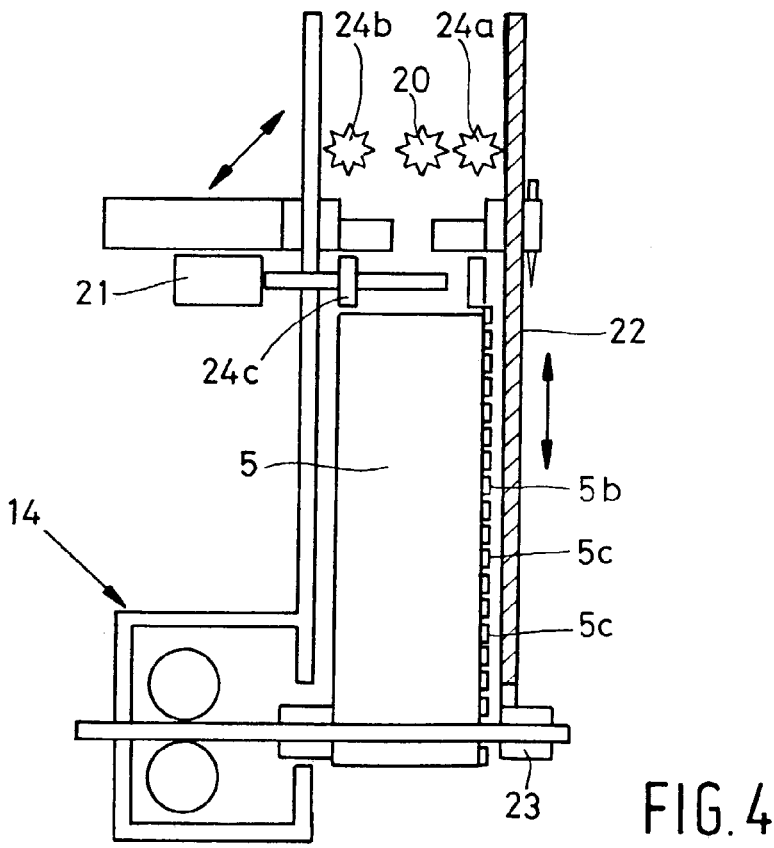

As disclosed in FIGS. 3-5 the adjusting means 13 are capable of exerting a force on the needle 10 to be inserted and more in particular the adjusting means 13 are capable of moving the needle in a direction perpendicular to the direction of insertion into the body 1 of the patient.

The adjusting means 13 comprise first and second drive means 20 and 21, wherein the first drive means 20 are arranged to move the needle in a vertical direction relative to the patients body 1, whilst the second drive means 21 are arranged to move the needle in a horizontal direction relative to the patients body 1.

Although in this embodiment the insertion of the needle 10 can be adjusted in two directions which are orthogonal to each other, and more simplified embodiment may incorporate only one drive means, for example the first drive means 20, for adjusting the needle in e.g. a vertical direction. Also only the second drive means 21 can be employed.

As shown in FIG. 3 an embodiment of the template 5 is provided with a plurality of guide holes 5*a* through which a needle 10 is positioned for insertion into the prostate gland 11 with the needle drive means 14. For adjusting the insertion of the needle 10 due to an occurred and observed deviation from the desired location in the prostate gland 11 the adjusting means 13 comprise a shaft 22 which with one end is connected to the first and second drive means 20 and 21. At its free end 22*b* said shaft is provided with a guide ring 23 through which the needle 10 to be inserted is guided. By actuating the shaft 22 in a vertical or horizontal direction by means of the drive means 20 and/or 21, the guide ring 23 exerts a force in the desired direction on the needle 10, which exertion forces are used to correct any deviation of the needle away from its desired position in the prostate gland 11.

For displacing the shaft 22 and the guide ring 23 for the purpose of adjusting the movement of the needle 10 in the prostate gland lithe drive means 20 and 21 are provided with toothed wheels 24*a*, 24*b* and 24*c*, which toothed wheels mesh with a corresponding toothing provided on the template 5 and the shaft 22. With this construction an accurate displacement of the template 5 and the shaft 22 can be obtained for adjusting the needle 10 towards its desired location in the prostate.

In FIG. 4 another embodiment of the template 5 is disclosed, wherein said template 5 is made of a flexible rubber material, for example silicone, without any guide holes as in the embodiment of FIG. 3. The needles to be inserted in or near the desired location in the animal body can be placed at any position in the rubber template 5. Therefore already known templates provided with a plurality of uniformly spaced apart guide holes for the needles to be inserted are no longer needed. By replacing such specially constructed and expensive templates by a template without guide holes a less constricted optimization method is obtained and the exact position of the needles determined with a real inverse brachy-therapy planning system can be adjusted using the drive means 20, 21 and the needle insertion means 14.

In another embodiment adjacent said silicone template 5 a metal plate 5*b* provided with a plurality of guide holes 5*bc* is placed for exercising a counter force on the needle 10, in case the template 5 is too flexible.

Figures 5A, 5B:
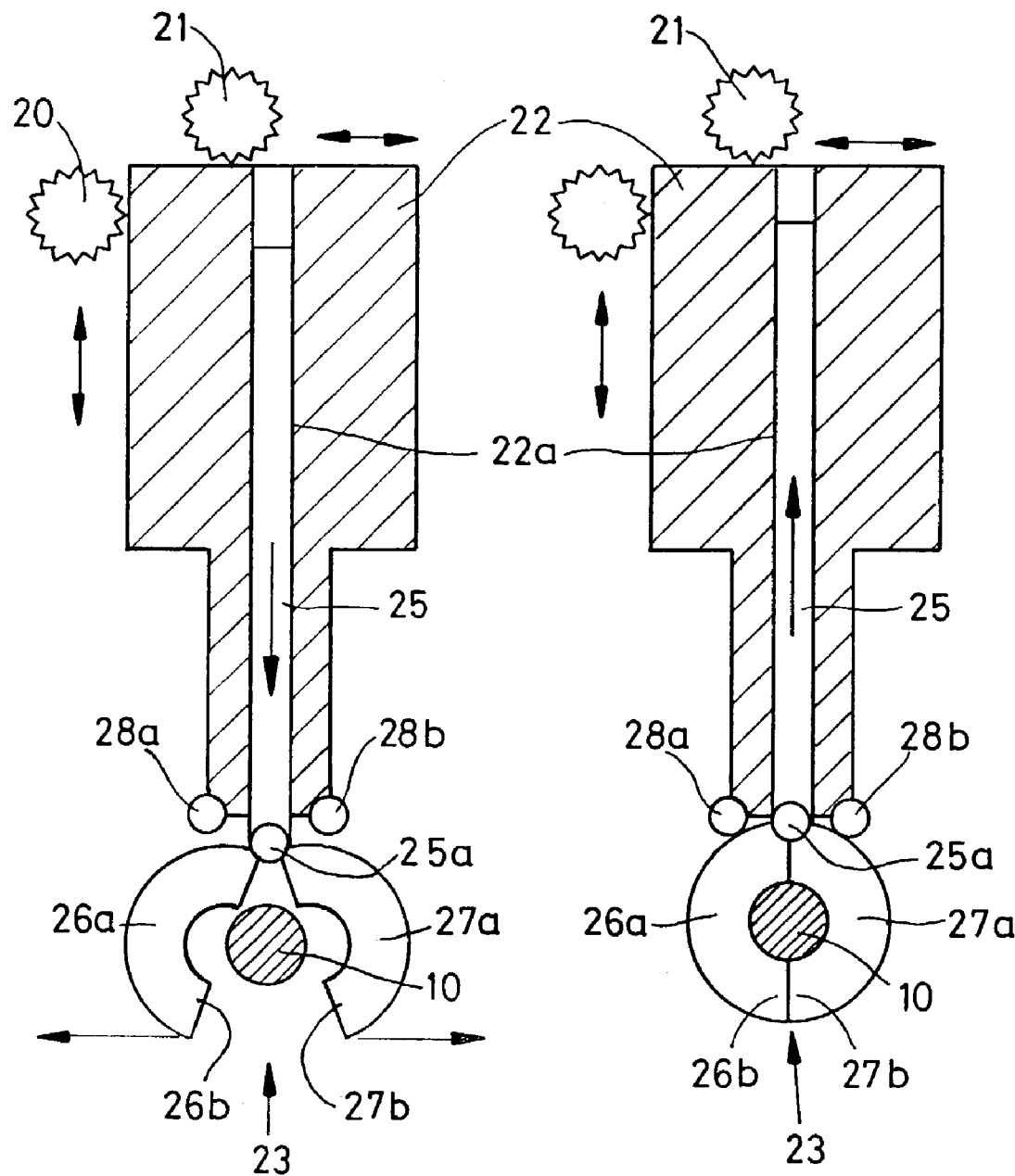

FIGS. 5A and 5B show in more detail the construction of the shaft 22 and the guide ring 23. In this preferred embodiment the shaft 22 is provided with a longitudinal hollow bore 22*a* wherein an actuator rod 25 is movable accommodated. Said actuator rod 25 can be moved in said hollow bore using suitable means, for example electromagnetic drive means (not depicted). Furthermore, the guide ring 23 comprises at least two ring parts 26 and 27 which with one end 26*a* and 27*a* respectively are connected to the free end 25*a* of said actuator. Preferably said connection has the form of a hinge allowing a movement of the ring parts 26 and 27 relative to the actuator rod 25 and each other.

Due to the fact that the at least two ring parts 26 and 27 can be moved relative to each other, they can be released from or placed around the needle 10 to be inserted. This situation is shown in FIG. 5A where a displacement of the actuator rod in downward vertical direction towards the needle 10 moves the free ends 26*b* and 27*b* of the two ring parts 26 and 27 away from each other, for example due to earth gravity. See also the arrows in FIG. 5A. The shaft 22 can now be placed around the needle 10 to be inserted by displacing the shaft 22 with the first vertical drive means 20.

Displacement of the actuator rod 25 in upward vertical direction as disclosed in FIG. 5B will bring the two ring parts 26 and 27 in contact with cams 28*a* and 28*b* mounted on the free end of the shaft 22 urging the free ends 26*b* and 27*b* of the two ring parts 26 and 27 towards each other thereby enclosing the needle 10.

The described method allows a continuous control of the tip 10*a* of the needle 10 during the insertion into an animal body and small deviations from the ideal direction will be corrected automatically with the two drive means or motors 20 and 21 and the needle 10 will be guided during the insertion. The two motors 20 and 21 are taking over the pressure, which is applied with an index finger of a person and will self control—based on the area analysis of the ultrasound image the insertion of the needles.

In the situation disclosed in FIG. 5B a new needle 10 to be inserted in the prostate gland 11 is now surrounded and guided by the guide ring 23 for adjusting purposes by the adjusting means 13.

Figure 6:
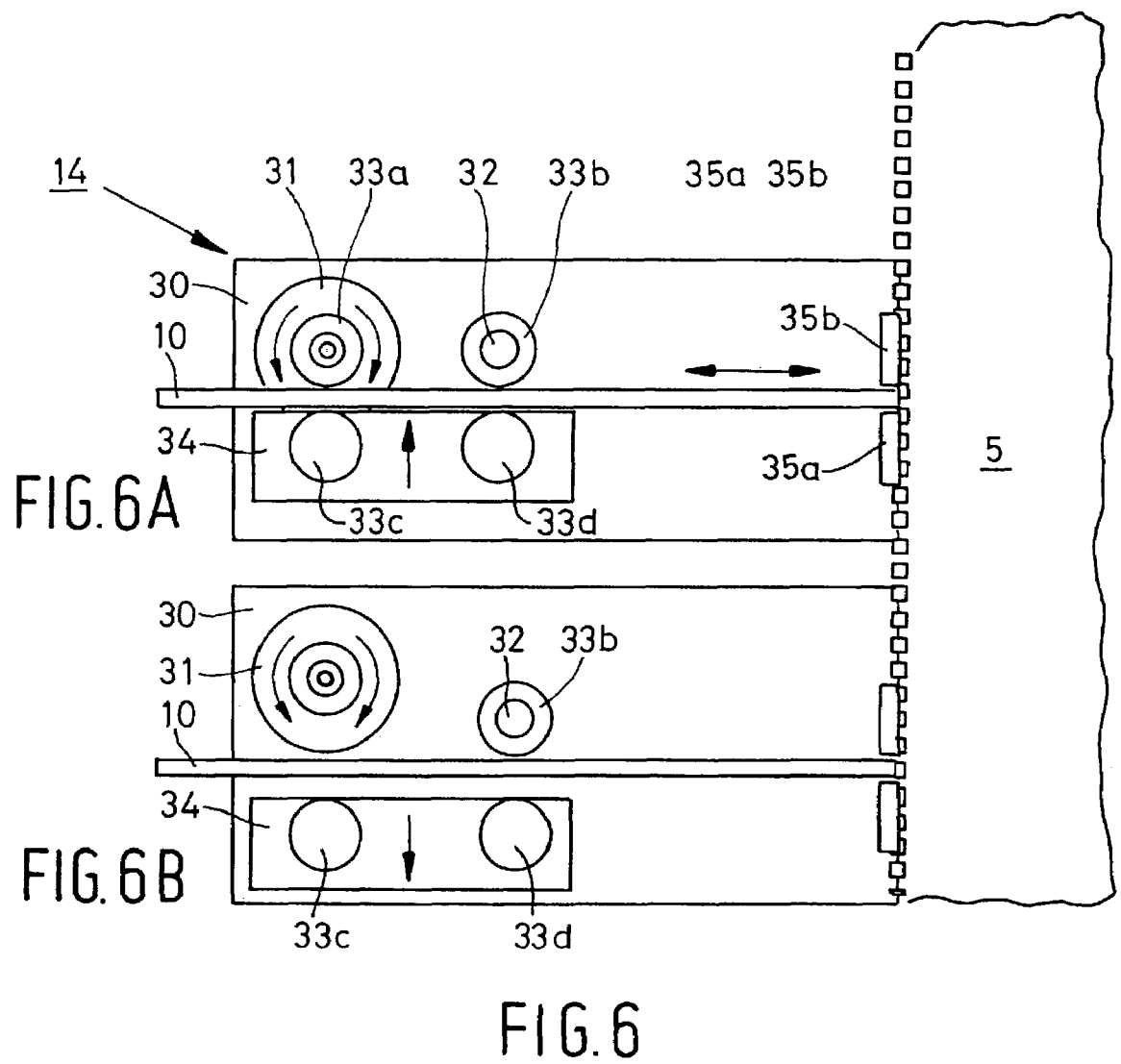

In FIG. 6 a specific embodiment of the needle insertion means 14 is disclosed. The needle insertion means comprise of a plate 30 with a motor 31 fixed on the plate 30 and an encoder device 32 also fixed on the plate. The needle 10 to be inserted is enclosed by four drive wheels 33*a*-33*d*, which are made of a hard rubber material. Said drive wheels 33*a*-33*d* are exchangeable, sterile and disposable and have to be replaced for each new patient and therapy. A movable plate 34 with the two drive-press wheels 33*c*-33*d* will allow the release of the needle 10 after the insertion. The movable plate 34 has two fixed positions, the first is disclosed in FIG. 6A and the second "release" position is shown in FIG. 6B. The movable plate can be positioned between these two fixed positions by means of suitable means (not shown), such as a stepping motor or an electric pushing and retracting device.

The needle insertion means 14 includes also means for determining and setting of a first initial reference or "zero" position for the needle tip. These means comprise a pair of optical sensors 35*a*-35*b* placed at or near the template 5. The position of said pair of sensors 35*a*-35*b* is important for the control of the insertion depth of the needle in the body and in the organ. In each case the distance of the pair of optical sensors from the template reference point has to be determined for each system and has to be known by the control means 15.

If the needle 10 is inserted until the desired and prescribed position the needle 10 is released from the needle insertion means 14 and from the guiding and adjusting means (13, 22, 22*b*, 23) as described above. With this construction every needle 10 can be released automatically from the needle drive means 14 and the adjusting means 13 (FIGS. 5A-5B) after insertion at the desired location in the prostate gland 11. A new needle 10 positioned at another reference point with respect to the template 5 and the body can now be brought in co-operating contact with the drive wheels 33*a*-33*d* and with the guide ring 23 (FIGS. 5A-5B) for adjustment purposes during the insertion of this further needle 10.

It will be clear from the above specification and the accompanying claims in combination with the drawings that the invention provides a self controlled image guided device and method for inserting a needle in an animal body, wherein needle divergence during insertion can be corrected such that said needle can be positioned more accurately at its desired location at or near the site of intended radiation therapy in said body, thus obtaining a more perfect match of the implanted needles with the desired, planned dosimetry pattern.

The invention claimed is:

1. Device for inserting at least one hollow needle to a desired location in an animal body for effecting radiation therapy in said body, comprising:
    a template for positioning at least one needle to be inserted,
    needle drive means for driving a needle through said template towards the desired location in the body,
    real-time imaging means for creating and presenting an image of the desired location and the position of said needle during the insertion of said needle, and
    means for adjusting a movement of said needle towards said desired location during insertion based on signals delivered by said imaging means.

2. Device according to claim 1, wherein said adjusting means are capable of exerting correction forces on said needle almost perpendicular to the direction of insertion.

3. Device according to claim 1, wherein said adjusting means are capable of moving said needle in a direction perpendicular to the direction of insertion.

4. Device according to claim 1, wherein said adjusting means can move said needle in two orthogonal directions.

5. Device according to claim 4, wherein said adjusting means comprises at least one drive means for moving said needle in at least one of said directions.

6. Device according to claim 5, wherein said adjusting means comprises a shaft connected to at least one drive means, which shaft is provided at its free end with a guide ring through which the needle to be inserted is guided.

7. Device according to claim 6, wherein said guide ring comprises at least two ring parts, which parts can be moved in order to be released from or to be placed around the needle to be inserted.

8. Device according to claim 7, wherein said shaft has a hollow, longitudinal bore through which an actuator rod is movably mounted for actuating said at least two ring parts.

9. Device according to claim 8, wherein said actuator rod is connected with one end of each of said at least two ring parts.

10. Device according to claim 8, wherein when said actuator rod is moved in a direction towards the needle, the free ends of said ring parts are moved away from each other.

11. Device according to claim 8, wherein when said actuator rod is moved in a direction away from the needle, the free ends the ring parts are moved towards each other.

12. Device according to claim 11, wherein said at least two ring parts abut against a cam mounted near the free end of said shaft.

13. Device according to claim 1, wherein said template is made of a flexible rubber material.

14. Device according to claim 13, wherein a metal plate is positioned near at least one side of said template and provided with a plurality of holes.

15. Device according to claim 1, wherein said needle drive means comprises a plate with a motor and at least one pair of opposing drive wheels.

16. Device according to claim 15, wherein at least one of said drive wheels is movable between a position where it is free from the needle and a position where it is in frictional contact with the needle to be inserted.

17. Device according to claim 15, wherein said needle drive means furthermore comprises sensing means for establishing a first reference position of the needle to be inserted.

18. Device according to claim 17, wherein said sensing means comprise at least one pair of optical sensors.

19. Device according to claim 1, wherein the insertion of the needle is terminated once the needle is inserted at the desired location in the body.

20. Method for inserting at least one hollow needle to a desired location in an animal for effecting radiation therapy in said body, comprising the steps of:
    positioning a needle near the animal body,
    inserting said needle towards the desired location in the body,
    imaging the desired location and the position of said needle during the insertion of said needle using real-time imaging means, and
    adjusting the insertion of said needle towards said desired location during insertion using signals delivered by said imaging means.

\* \* \* \* \*